United States Patent [19]
Kern

[11] Patent Number: 5,861,505
[45] Date of Patent: Jan. 19, 1999

[54] SYNTHETIC ANALOG OF SIALIC LEWIS ANTIGEN FROM BACTERIAL CAPSULAR POLYSACCHARIDE

[75] Inventor: Roger G. Kern, Pasadena, Calif.

[73] Assignee: California Institute of Technology, Pasadena, Calif.

[21] Appl. No.: 724,337

[22] Filed: Oct. 1, 1996

Related U.S. Application Data

[63] Continuation of Ser. No. 277,173, Jul. 19, 1994, abandoned, which is a continuation-in-part of Ser. No. 799,419, Nov. 27, 1991, Pat. No. 5,330,903.

[51] Int. Cl.⁶ .............................. C07H 5/04; C12P 19/26
[52] U.S. Cl. ........................ 536/53; 536/55; 536/55.1; 536/55.2; 536/55.3; 536/123.1; 435/72; 435/84
[58] Field of Search ................... 536/55, 55.1, 123.1, 536/53, 55.2, 55.3; 435/72, 84

[56] References Cited

PUBLICATIONS

Carbohydrate Res., vol. 103, No. 1, pp. 107–128, Dutton et al. (1982).

Carbohydrtae Res., vol. 97, No. 1, pp. 127–138, Dutton et al., 127–138 (1981).

PNAS. vol. 88, Tyrrell et al., pp. 10372–10376. (1991).

"Structural Mofidication Of Polysaccharides: A Biochemical–Genetic Approach" Paper presented Dec. 1991., R.G. Kern and G. R. Petersen.

*Primary Examiner*—Kathleen K. Fonda
*Attorney, Agent, or Firm*—Graham & James LLP

[57] ABSTRACT

An analog of sialic Lewis antigen prepared from native capsular polysaccharide of Klebsiella 63 bacteria.

2 Claims, No Drawings

SYNTHETIC ANALOG OF SIALIC LEWIS ANTIGEN FROM BACTERIAL CAPSULAR POLYSACCHARIDE

This is a continuation of application Ser. No. 08/277,173 filed on Jul. 19, 1994 and now abandoned, which is a continuation-in-part of Ser. No. 07/799,419 filed Nov. 27, 1991, now U.S. Pat. No. 5,330,903.

The invention described herein was made in the performance of work under a NASA contract, and is subject to the provisions of Public Law 96-517 (35 U.S.C. § 202) in which the Contractor has elected to retain title.

This invention relates to novel and useful complex oligosaccharides and methods for producing them. More particularly, this invention relates to an analogue of sialic Lewis antigen prepared from native capsular polysaccharide of Klebsiella 63 bacteria.

BACKGROUND OF THE INVENTION

Complex polysaccharides have a variety of industrial applications. Generally these molecules alter the physical properties——including viscosity and rheology——of fluid media in which they are suspended. Accordingly, complex polysaccharides are used as thickeners in the food industry, for suspending waste fragments in drilling or cutting operations, and as water soluble lubricants. Baird et al., "Industrial Applications Of Some New Microbial Polysaccharides," *Biotechnology*, November 1983, pp. 778–83. For similar reasons, complex polysaccharides are also used to reduce turbulence of fluid flow in pipelines and other containers. J.W. Hoyt, Drag Reduction In Polysaccharide Solutions, *Trends In Biotechnology*, 3, 17–20 (1985). The physics-chemical basis for these effects is not understood, id. although correlations between drag reduction and the extensional viscosity of polysaccharides have been reported. G.R. Petersen et al., "Rheologically Interesting Polysaccharides From Yeasts", *Appl. Biochem. Biotech.*, 20/21, 845–67 (1989).

Because the basis for these useful properties of complex polysaccharides is not understood, the identification of useful complex polysaccharides requires screening of candidate polymers. Accordingly, it is desirable to develop methods for producing new candidate complex polysaccharides for evaluation.

Structurally altered capsular polysaccharides are produced by mutant bacteria. These polysaccharides are isolated by selecting a wild type bacterial strain and a phage producing degradative enzymes that have substrate specificity for the capsular polysaccharides produced by the wild type bacteria. Phage-resistant mutants producing capsular polysaccharides are selected and the structurally altered capsular poly saccharide is isolated therefrom.

The cells of many bacterial species specifically, gram negative bacteria——are surrounded by a glycocalyx also referred to as a capsular polysaccharide ("CPS") several hundred nanometers in thickness. The glycocalyx consists of a complex polysaccharide polymer that appears to be species specific. H. Geyer et al. "Degradation Of Bacterial Surface Carbohydrates By Virus-Associated Enzymes", *Pure and Applied Chemistry*, 55, pp. 673–85. Hence bacteria have proved to be an important source of complex polysaccharides. Baird et al. (1983). Bacteria are an especially desirable source of polysaccharides because of the purity and uniformity of the product.

Bacteriophage are viruses that infect bacteria. The viruses that infect bacteria encapsulated by a glycocalyx are specially adapted to penetrate the polysaccharide barrier. The tail fibers or spikes by which these viruses are seen to attach to bacteria contain enzymes——generally referred to as endoglycanases or endopolysaccharases——that degrade the glycocalyx. These enzymes exhibit a high degree of substrate specificity. Geyer et al, *Pure and Applied Chemistry*, 55, pp. 673–85.

According to the present invention, a strain of encapsulated bacteria and the specific phage which infects it are employed. The selected bacteria are optionally exposed to a mutagenic agent. Examples of useful mutagenic agents include radiation and chemical mutagens, such as nitrosoguanidine. The mutagenized bacterial cells are grown to a desired density, and then screened for resistance to phage that specifically degrade the glycocalyx of the wild type strain surviving bacteria are likely to have a glycocalyx with altered chemical structure. The CPS of the selected bacterial strains is harvested with enzymes derived from phage. The isolated CPS is purified by known techniques and degraded to oligomer by further treatment with phage enzymes.

In one embodiment of the present invention, we employed a strain Klebsiella pneumoniae that produces a capsular polysaccharide known as K63, and a phage ("K63 phage") that specifically degrades the same polysaccharide. We obtained Klebsielia pneumoniae strain 5845/52 from the World Health Organization. This strain produces the K63 capsular protein. The K63 CPS is a straight chain heteropolymer of fucose, galacuronic acid and galactose, linked, in that order by a 1–3 glycosidic linkages. The K63 phage enzymatically hydrolyzes the a 1–3 linkage between the galactose and fucose monomers. Both the nature of the CPS polymer and the mode of action of the K63 phage enzyme are representative, and support the general applicability of our method.

We selected mutants for further study that were either spontaneously generated or were induced by exposure to the mutagenic agents nitrosoguanidine or ultraviolet radiation. J.H. Miller, *Experiments In Molecular Genetics* (1972). Following treatment to induce mutation, cells were grown on DIFCO Nutrient Broth, supplemented with 1% glucose, at 30° C., while rotated at 150 rpm. Cells were grown to early stationary phase ($OD^{590}$ of approximately 3.5). Calcium chloride (0.1M) was added to stabilize the CPS matrix.

The fresh stationary phase culture, less than 2 hours old, contained approximately $2.5 \times 10^9$ viable cells/ml. Phage 63 was added at a concentration sufficient to achieve a multiplicity of infection ("MOI") of between one and five. The culture was incubated at room temperature for about 10 minutes to permit phage to attach to the bacterial cells. The infected culture was then diluted 10 fold into fresh glucose supplemented nutrient broth and grown overnight to stationary phase. Phage resistant mutants were isolated as single colonies on petri dishes after streaking with the overnight culture of infected bacteria. Resistant colonies that did not form plaques were selected. Phage resistance of the selected colonies was confirmed by administration of a drop of phage/enzyme concentrate. The zone of lysis produced by the diffusion of the phage/enzyme concentrate was dramatically reduced for those strains with phage resistance when compared with wild type bacteria.

Mutants whose phage resistance was due to altered CPS were selected from among those phage resistant mutants already identified. The phage resistant colonies were grown for 5 to 7 days so that mucoid (CPS producing) and non-mucoid mutant colonies could be distinguished. The colonies were retested for phage resistance as before. Mucoid mutants that remained phage resistant were assumed to have altered CPS. Non-mucoid phage resistant mutants were assumed to be resistant for other reasons, for example, lacking virus receptor sites. Approximately 90% of the 5845/52 phage resistant mutants have altered CPS by this criterion.

In order to test the capacity of the altered CPS from mutant cells to affect Theological properties of aqueous media, we partially purified the CPS. The cultured mutant bacterial cells, like those produced by large-scale industrial fermentations, is resistant to high speed centrifugation. We succeeded in achieving substantial purification of the altered CPS using a concentrated extract of phage enzymes.

A concentrated mixture of CPS specific enzyme and phage fragments was prepared by preparing a phage lysate from stationary phase cultures, and concentrating the lysate 80 fold with an AMICON hollow fiber filter (HPI10), followed by dialysis to remove low molecular weight substances. The final concentration factor was 39. This material showed a 24-fold enhancement in enzymatic activity as determined by a reducing end sugar assay, as compared with crude phage lysate.

Phage/enzyme concentrate was added in small quantities——1 ml/liter——to cultures of mutant bacterial cells. This results in a rapid and dramatic reduction (>100 fold) in the viscosity of the culture media. Altered CPS was thereafter separated from the bacterial cells by low speed centrifugation at 20 degrees C. Immediately after centrifugation, the supernatant was precipitated by the addition of 4 volumes of isopropanol at 20 degrees C. We have also used cold ethanol in place of cold isopropanol. The resulting precipitate was rehydrated and extensively dialyzed against deionized water.

The CPS polymer obtained from wild-type K63 bacteria had an apparent molecular weight of 3.5×10 6 daltons. Digestion of this material with phage 63 enzyme reproducibly yielded a homogeneous monodisperse polysaccharide with a molecular weight of 9.0–105 daltons.

We measured the drag reduction produced by undigested CPS harvested from wild type and mutant K63 bacteria using a turbulent flow rheometer fabricated according to the design of Hoyt (J.W. Hoyt, *Polymer Letts.,* 9, 851–62 (1971); J.W. Hoyt, "The Solution Properties Of Natural Polymers", *The Chemical Society Special Publication*, No. 23, (London) pp. 86–91 (1968)] modified by altering pipe diameter to operate at a fixed Reynolds number of 16,500. The drag reduction was calculated:

$$\text{Drag Reduction } (\%) = 100 \times (PD_{solvent} - PD_{solution}) / PD_{solvent}$$

Where are $PD_{solvent}$ and $PD_{solution}$ the pressure differences in the solvent and solution, respectively, measured from a strip chart recording of pressures taken at two points, 12.7 cm apart, along a 1 mm pipe. Between sample runs, the rheometer was rinsed with tap water until the baseline returned to normal. Sample size was 100 ml and all measurements were made with water as the solvent. Sample observations were normalized (wt/ppm or mg/1) typically 100–500 wt/ppm. Our observations were reproducible to within 1–2%. We considered measurements that differed by less than 5% to be equivalent.

Our observations of drag reduction coefficients for wild type and mutant CPS (from 8 mutant strains) are summarized in Table 1. Mutant strains 1, 2 and 5 were spontaneous mutants, while strains 3, 4, 5, 6, and 8 were induced by nitrosoguanidine. All mutants showed a decrease in pyruvulation while altered NMR spectra have been detected only in the spontaneous mutants. Our results show a 10% improvement in drag reduction in the CPS from mutant bacteria. Furthermore, as also shown in Table 1, CPS from mutant bacteria is more resistant to mechanical shearing as determined by repeated observations of drag reduction with a rheometer.

TABLE 1

Characterization of K63 CPS Mutants: Drag Reduction Results

| STRAIN | % DRAG REDUCTION | % SHEAR STABILITY |
|---|---|---|
| K 63 wt | 55.9 | 84.9 |
| K 63-JPL1 | 67.7 | 95.6 |
| K 63-JPL2 | 66.7 | 95.6 |
| K 63-JPL3 | 67.0 | 99.4 |
| K 63-JPL4 | 67.6 | 98.2 |
| K 63-JPL5 | 67.0 | 99.4 |
| K 63-JPL6 | 67.6 | 95.7 |
| K 63-JPL8 | 67.2 | 99.7 |

Bacteria are also a useful source of polysaccharides that can be chemically modified for further synthesis. For example the Klebsiella K63 model system can be used as a source of an analogue of the Sialyl Lewis X Antigen ("SLe X"). SleX is a tetrasaccharide which is known to inhibit inflammation in mammals. Its mode of action is believed to be blocking adhesion of neutrophils or leukocytes (cellular components of blood involved in the inflammatory process) to binding sites termed "Selectins", particularly, Selectin E, on the surface of endothelial cells. [Y. Ichikawa "Chemical-Enzymatic Synthesis and Conformational Analysis of Sialyl Lewis x and Derivatives", *J.Am. Chem Soc.* 1992, 114, 9283–9298] This therapeutic approach has application in limiting reperfusion injury following myocardial infarction, surgery and traumatic shock.

De novo synthesis of oligosaccharides using chemical methods is problematic. Chemical synthesis of each monomeric component requires about 7 separate steps; for a tetrasaccharide, nearly 30 steps would be required. Chemical synthesis is expensive and time consuming even when carried out by an experienced scientist. It is believed that chemical synthesis of short chain oligosaccarides would cost about $75,000. per gram of product. Accordingly, chemical modification of naturally occurring oligosacharrides represents a significant savings in time and material.

SUMMARY OF INVENTION

An analogue of sialic Lewis antigen prepared from native capsular polysaccharide of Klebsiella 63 bacteria.

DETAILED DESCRIPTION

The structure of the native $Sle^{X}$ oligosaccharide is:

αNeuAc-β(2–3)-Gal-β(1–4)-GLcNHAc-α(1–3)-Fuc.

Where αNeuAc is N acetylneuraminic acid, also known as sialic acid; Gal is galactose; GLcNHAc is N-Acetylglucosamine and Fuc is fucose. [Y. Ichikawa "Chemical-Enzymatic Synthesis and Conformational Analysis of Sialyl Lewis x and Derivatives", *j. Am. Chem. Soc.* 114, 9283–9298]. Those portions of SLeX believed to be important in binding to E seletins are shown in bold face:

αNeuAc-β(2–3)-Gal-β(1–4)-GLcNHAc-α(1–3)-Fuc.

The repeating unit of the straight chain heteropolymer of the naturally occurring capsular polysaccharide produced by Klebsiella K63 has a similar sequence:

Gal-α(1–3)-GalA-α(1–3)-Fuc, where the identical monomers are underlined. Enzymatic addition of sialic acid would result in an analogue to SLe x with the structure:

αNeuAc-β(2–3)-Gal-α(1–3)-GalA-α(1–3)-Fuc, where common monomers are again underlined. The structure would include all elements believed to be involved in the binding of $SLe^X$ to Selectin E. On the other hand, the galacturonic acid monomer may be substituted by X, where X can be any sugar monomer residue, or glycosidic linkage, produced as a result of phage K63 selection of altered CPS producing Klebsiella K63 mutants. Other sugar monomer residues may include, but are not limited to: hexuronic acids (eg. glucuronic acid), hexoses (eg. glucose) or amino sugars and their derivatives (eg. N-acetylgucosamine). In view of the structural similarities between the analogue and $SLe^X$, it is believed that the analog would have clinical efficacy in inhibiting inflammation.

EXAMPLE

Capsular polysaccharide is obtained from Klebsiella Pneumoniae capsular serotype K63 as previously described. Freshly harvested wild type bacterial cells are treated with concentrated K 63 phage lysate. The CPS is separated from the cells by low speed centrifugation followed by precipitation with cold isopropanol. The CPS is then exhaustively digested with concentrated K 63 phage lysate. Specifically 1 ml of the previously described phage / enzyme concentrate is added to 1 gram of bacterial CPS dissolved in 300 ml of distilled water. The endoglycanase reaction is allowed to proceed for 72 hours at 37 degrees C. This process results in the conversion of 66% of the CPS to its single repeat unit oligosaccharide trimer with 33% remaining as higher molecular weight oligosaccharide. Following concentration of the reaction mix by lyophilization the trimer is purified by molecular exclusion chromatography. The result is the trimer:

Gal-α(1–3)-GalA-α(1–3)-Fuc.

Sialic acid is added to the trimer by an a(2-3) linkage to the non-reducing galactose terminal residue of the trimer, to produce an analog of $SLe^X$.

This reaction is effected by an exoglycosidase. Although these enzymes normally catalyze the hydrolytic removal of a specific sugar monomer from the non-reducing terminus of an oligosaccharide, the reaction can be forced to operate in reverse using a high concentration of monosaccharide along with increased temperature. [Y. Yoshitaka, "Enzyme-Catalyzed Oligosaccharide Synthesis" et al., *Anal. Biochem.*, 202, pp. 215–18 (1992).]

One unit of neuraminidase (*A. ureafaciens* EC 3.2.1.24; *C. perfrigens* EC 3.2.1.18; new castle disease virus, Hitchner B1 strain EC 3.2.1.18 or *V. cholera* EC 3.2.1.18 are used—all available from Boehringer Mannheim) is added to 200 mg. sialic acid and 10 mg. k63 trimeric oligomer. Reaction is permitted to proceed for 18 hours at 37 degrees C in 100 mM citrate buffer. pH is adjusted to 4.5 for neuraminidase from *A. ureafaciens,* 5.0 for neuraminidase from *C. perfrigens*, and 5.5 for neuraminidase from new castle disease virus and *V. cholera*. Reaction is terminated by heating to 90 degrees C. for 2 minutes. The $SLe^X$ analog is purified by molecular exclusion chromatography.

This example is for the purposes of illustration only, and is not intended to limit the scope of applicant's invention.

I claim:

1. An analog of sialic Lewis antigen of the structure:

αNeuAc-β(2–3)-Gal-α(1–3)-GalA-α(1–3)-Fuc.

2. A method for producing synthetic sialic Lewis antigen analogue comprising the steps of:
   a) isolating capsular polysaccharide of Klebsiella K 63;
   b) exhaustively digesting the isolated capsular polysaccharide of Klebsiella K 63 with K63 phage lysate;
   c) adding sialic acid to the non-reducing terminus of the galactose monomer of the exhaustively digested capsular polysaccharide of step b) above; and
   d) purifying the resulting tetramer.

* * * * *